(12) United States Patent
Sardo

(10) Patent No.: US 9,950,087 B2
(45) Date of Patent: Apr. 24, 2018

(54) DEVICE FOR EVAPORATING A LIQUID AND RELATED METHOD

(71) Applicant: XEDA INTERNATIONAL, Saint Andiol (FR)

(72) Inventor: Alberto Sardo, Chateaurenard (FR)

(73) Assignee: XEDA INTERNATIONAL, Saint Andiol (FR)

( * ) Notice: Subject to any disclaimer, the term of this patent is extended or adjusted under 35 U.S.C. 154(b) by 0 days.

(21) Appl. No.: 14/879,417

(22) Filed: Oct. 9, 2015

(65) Prior Publication Data

US 2016/0030615 A1 Feb. 4, 2016

Related U.S. Application Data

(63) Continuation-in-part of application No. 13/845,281, filed on Mar. 18, 2013, now abandoned.

(30) Foreign Application Priority Data

Jun. 25, 2012 (FR) .................................... 12 55999

(51) Int. Cl.

| B01F 3/04 | (2006.01) |
|---|---|
| A61L 2/20 | (2006.01) |
| B01B 1/00 | (2006.01) |
| A61L 9/12 | (2006.01) |
| B01D 1/14 | (2006.01) |
| B01D 3/34 | (2006.01) |

(52) U.S. Cl.
CPC ................. *A61L 2/20* (2013.01); *A61L 9/122* (2013.01); *A61L 9/127* (2013.01); *B01B 1/005* (2013.01); *B01D 1/14* (2013.01); *B01D 3/346* (2013.01)

(58) Field of Classification Search
CPC . A61L 2/20; A61L 9/122; A61L 9/127; B01B 1/005; B01D 1/14; B01D 3/346
USPC ................. 261/23.1, 28, 103, 104, 106, 107
See application file for complete search history.

(56) References Cited

U.S. PATENT DOCUMENTS

| 161,062 A | 3/1875 | Satterlee |
|---|---|---|
| 282,474 A | 7/1883 | Von Cort |
| 907,811 A | 12/1908 | Jordan |
| 1,241,376 A | 9/1917 | Hanson |
| 1,750,047 A | 3/1930 | Metzger |
| 1,962,532 A | 6/1934 | Strong |
| 3,092,096 A | 6/1963 | Nett et al. |
| 3,139,462 A | 6/1964 | Scott et al. |

(Continued)

FOREIGN PATENT DOCUMENTS

| FR | 2791910 | 10/2000 |
|---|---|---|
| FR | 2992225 | 12/2013 |
| WO | 2009144465 | 12/2009 |

*Primary Examiner* — Charles Bushey
(74) *Attorney, Agent, or Firm* — Davidson, Davidson & Kappel, LLC

(57) ABSTRACT

A biocidal treatment evaporates a liquid having biocidal properties. An absorption organ has absorbent strips suited to retain the liquid, each absorbent strip having a top first end and a bottom second end, The liquid is injected into the first end of each absorbent strip, the liquid flowing by gravity along the absorbent strip towards the second end, the liquid having biocidal properties being injected at a predetermined flow rate. The liquid is evaporated by producing a gas flow directed towards the absorption organ at a temperature below 50° C.

**18

(56) References Cited

U.S. PATENT DOCUMENTS

Figure 1:
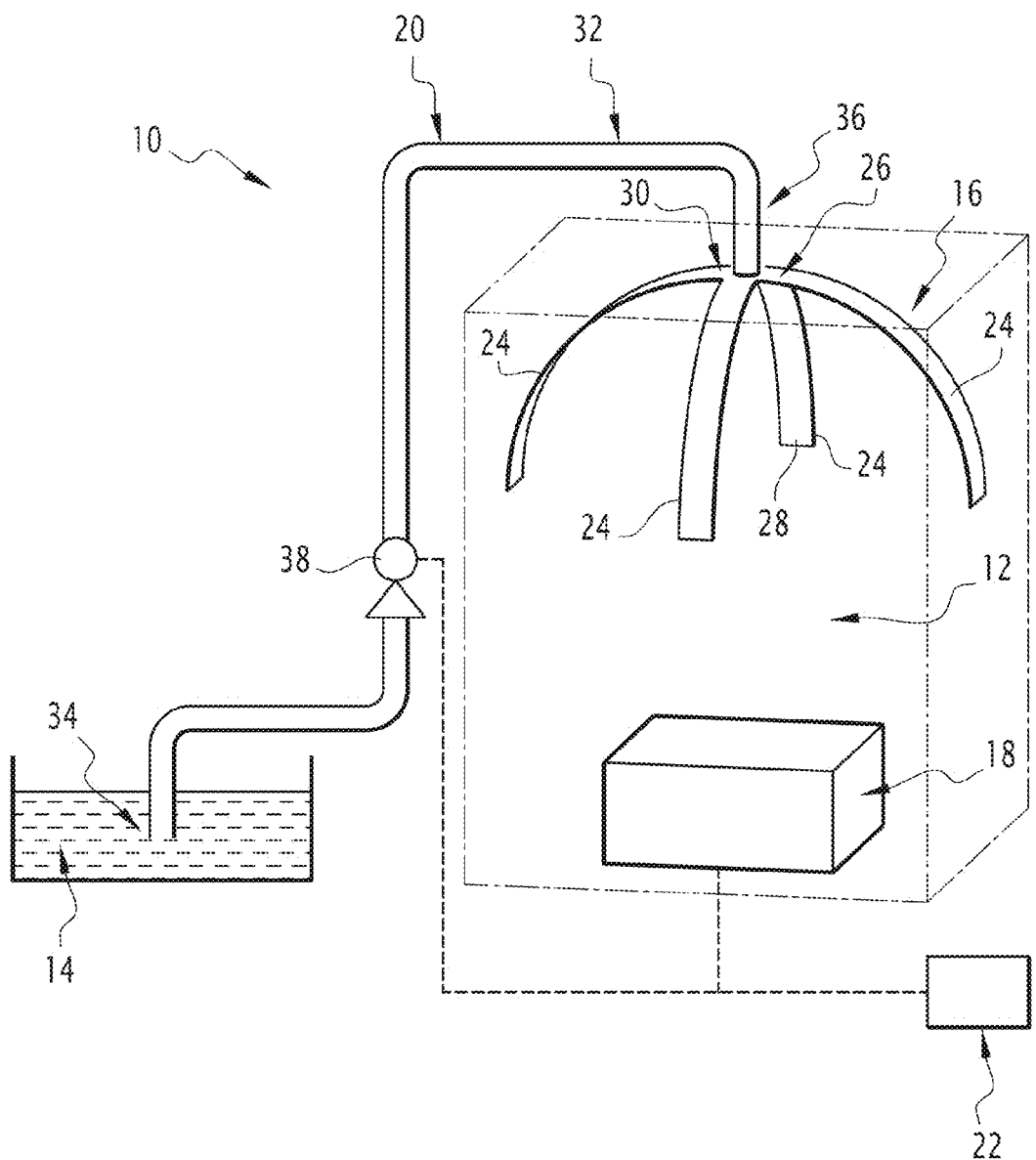

| | | | | |
|---|---|---|---|---|
| 3,748,828 A | * | 7/1973 | Lefebvre | B01D 1/14 |
| | | | | 210/635 |
| 5,168,832 A | | 12/1992 | Price | |
| 5,203,505 A | | 4/1993 | Yum | |
| 5,911,742 A | * | 6/1999 | Akazawa | A61L 9/12 |
| | | | | 165/41 |
| 6,109,539 A | * | 8/2000 | Joshi | A01M 1/2033 |
| | | | | 239/43 |
| 6,631,891 B1 | * | 10/2003 | Slade | A61L 9/127 |
| | | | | 239/44 |
| 8,080,127 B2 | * | 12/2011 | Chen | B01D 1/14 |
| | | | | 159/16.1 |
| 8,672,235 B2 | * | 3/2014 | Sardo | A23B 7/153 |
| | | | | 137/113 |
| 9,072,291 B2 | * | 7/2015 | Sardo | A01N 3/00 |
| 2013/0087043 A1 | * | 4/2013 | Enzenhofer | B01D 1/065 |
| | | | | 95/257 |
| 2013/0341809 A1 | | 12/2013 | Sardo | |

\* cited by examiner

US 9,950,087 B2

DEVICE FOR EVAPORATING A LIQUID AND RELATED METHOD

This application is a continuation in parts of U.S. application Ser. No. 13/845,281, filed Mar. 18, 2013, which became abandoned on Oct. 22, 2015, which claims priority of French application FR 12 55999, filed Jun. 25, 2012, the entire contents of which is incorporated by reference.

BACKGROUND OF THE INVENTION

Field of the Invention

This invention generally concerns devices allowing for sterilisation treatment, in particular by a vapor of essential oils or volatile synthetic products intended for sites or plant matter. In the case of food products such as fruits and vegetables, the treatment seeks to extend their preservation. In the case of sites, the treatment seeks to sanitise them.

This invention further concerns devices to increase the humidity of sites or rooms for storing plant matter.

Description of the Related Art

WO 2009/144465 describes the possibility of using essential oil vapours, e.g., essential oils extracted from citrus fruits, to treat fresh foods and destroy or inhibit the growth of microorganisms contaminating those foods.

The industrial treatment of food products such as fruits and vegetables stored in storerooms, greenhouses, or silos requires the production of substantial amounts of vapour. Furthermore, the vapours must not condense and form droplets of essential oils, volatile synthetic products, or water, which may settle on the food products. Such settled condensation may in fact be phytotoxic.

In this context, there is a need for a device that can produce substantial quantities of vapour without any risk of condensation.

SUMMARY OF THE INVENTION

To this end, the invention, according to a first aspect, concerns a device for evaporating a liquid, including:
  a reservoir containing the liquid;
  an organ for absorbing the liquid; and
  an organ for producing a gas flow, which is directed towards the absorption organ;
  characterised in that the absorption organ comprises a plurality of absorbent strips suited to retain the liquid.

The fact that the absorption organ comprises a plurality of absorbent strips forms a substantial contact surface between the gas flow and the absorption organ, and thus a substantial surface for evaporating the liquid. Furthermore, the absorbent strips are advantageously spaced such that the absorption organ is suited to provide a substantial space for the passage of the gas flow. Thus, the device according to the invention allows for the evaporation of a substantial quantity of liquid.

Typically, the liquid comprises at least one essential oil. For example, the liquid includes an essential oil chosen from the group of mint oil, thyme oil, oregano oil. In one variant, the liquid comprises one of the constituents of these oils, c hosen from L-carvone, eugenol, geraniol, thymol, or carvacrol.

In one variant, the liquid comprises at least one volatile synthesis product with biocidal properties, such as dimethyl naphthalene, 3-decene-2-one, or hexanal.

In one variant, the liquid composition includes pyrethrum or synthetic pyrethrins, or any volatile synthetic molecules with biocidal properties.

Typically, the liquid includes only one active ingredient with no solvent or adjuvant.

"Active ingredient" refers to an essential oil or volatile synthesis product.

In one variant, the liquid includes an aqueous or organic solvent, in which the active ingredient and/or one or more adjuvants is dissolved. The aqueous solvent is, e.g., water. The organic solvent is, e.g., a solvent of the type described in FR 2791910 or glycols, diglycols, and their respective esters The adjuvants are, e.g., substances suited to transport the active ingredient(s) or provide a diluting effect.

In one variant, the liquid includes a mixture of several liquid active ingredients, e.g., several essential oils from the list above, or several synthesis products from the list above.

In one variant, the liquid includes only water. In this case, the vaporisation of the liquid water by the evaporation device according to the invention is intended to increase the humidity of the storage area or room for plant matter in which the liquid is vaporised.

Typically, the device is suited to vaporise the liquid at a temperature below 50° C., i.e., the gas flow is at a temperature below 50° C., preferably below 20° C., in particular between -2° C. and 12° C., and in particular between 0 and 10° C. The gas flow is, e.g., at room temperature. The device according to the invention thus allows for evaporation of the liquid without the need for heating means. The device according to the invention does not require nozzles to inject the liquid at high pressure, which generally involve high installation costs and do not avoid later condensation of the evaporated liquid.

Typically, each strip consists of plant microfibres. In one variant, each strip consists of synthetic fibres. Each strip consists, e.g., of 80% polyester and 20% polyimide.

According to a first embodiment, the device comprises an organ for injecting the liquid into the absorption organ from the reservoir. "Injection" here refers to the act of introducing, by a voluntary, affirmative action, a quantity of liquid into the absorption organ.

Preferably, the injection organ comprises a dosing pump. Such a dosing organ allows for precise control of the quantity of liquid injected. In one variant, the liquid is injected by gravity, by the Venturi effect, or by any other suitable dosing organ.

Typically, the dosing pump and the gas flow production organ are controlled by a computer. In one variant, the dosing pump and/or the gas flow production organ are controlled manually.

According to this first embodiment, each strip has a first end and a second end, and the injection organ has a liquid injection output arranged near the first end of each strip. Thus, the liquid is injected into the first end of each strip, and flows due to gravity along each absorbent strip towards the second end.

According to this first embodiment, the first end of each strip is typically arranged at the pole of a sphere, with each strip extending from the pole along a longitude of the sphere. This configuration allows for optimisation of the evaporation of the liquid retained in the absorbent strips. In one variant, the absorption organ has a conical, potato-shaped, or any concave shape.

According to this first embodiment, the gas flow production organ is aimed at the pole on the concave side of the sphere. This arrangement of the gas flow production organ with respect to the absorption organ allows the gas flow to be directed so as to optimise the evaporation of the liquid.

In fact, it allows for better distribution of the air flow compared to the absorbent strips that retain the liquid to be evaporated.

The gas flow production organ is, e.g., a fan.

According to a second embodiment, the absorbent strips are arranged parallel to one another and extend along a longitudinal axis, which is perpendicular to the direction of the gas flow. In one variant, the longitudinal axis is inclined with respect to the direction of the gas flow.

According to the second embodiment, the device comprises a liquid storage organ connected to the reservoir, with the second end of each strip soaking in the liquid of the storage organ such that each strip absorbs the liquid by capillarity.

According to this second embodiment, the device comprises a tube for injection from the reservoir to the liquid storage organ. Typically, and like the injection organ of the first embodiment, the injection tube comprises a dosing pump.

According one variant of the second embodiment, like the first embodiment, the device comprises an organ for injecting the liquid into the absorption organ from the reservoir.

According to this variant, each strip has a first end and a second end, and the injection organ has a liquid injection output arranged near the first end of each strip. Thus, the liquid is injected into the first end of each vertical absorption strip, and flows due to gravity along each vertical absorbent strip.

According to a second aspect, the invention concerns an assembly for treating a site, comprising:
A site; and
An evaporation device according to any of the foregoing claims.

According to a third aspect, the invention concerns a method for evaporating a liquid, comprising the following steps:
Absorption of the liquid by an absorption organ comprises a plurality of absorbent strips suited to retain the liquid;
Production of a gas flow, which is directed towards the absorption organ;
Evaporation of the liquid at a temperature below 50° C.

BRIEF DESCRIPTION OF THE DRAWING FIGURES

Other characteristics and benefits of the invention can be seen from the detailed description provided below, by way of example only, in reference to the attached drawings, of which:

FIG. 1 is a simplified schematic representation of an assembly for treating a site comprising a first embodiment of a liquid evaporation device according to a first embodiment of the invention;

FIG. 2 is a simplified schematic representation of an assembly for treating a site comprising a second embodiment of a liquid evaporation device according to a first embodiment of the invention; and FIG. 3 is a simplified schematic representation of a variant of the first embodiment.

FIG. 4 is a simplified schematic representation of a variant of the second embodiment.

DETAILED DESCRIPTION OF THE INVENTION

FIG. 1 is a perspective view of a device 10 for evaporating a liquid according to a first embodiment of the invention.

Such a device 10 is typically provided for the sterilisation of a site 12 or a storeroom for plant matter such as a greenhouse, if the liquid to evaporate contains at least one essential oil. If the liquid to be evaporated only comprises water, such a device 10 is provided to increase the humidity of the site 12 or the storeroom.

The device 10 shown in FIG. 1 comprises:

a reservoir 14 containing the liquid;

an organ 16 for absorbing the liquid;

an organ 18 for producing a gas flow;

an organ 20 for injecting the liquid, suited to inject the liquid into the absorption organ 16 from the reservoir 14; and a computer 22 controlling the injection organ 20 and the gas flow production organ 18.

According to the invention, the absorption organ 16 comprises a plurality of absorbent strips 24 suited to retain the liquid. For example, the absorption organ includes between 2 and 40 absorbent strips, in particular 4-20 strips, and in particular 6-10 strips.

The absorbent strips 24 of the absorption organ 16 consist, e.g., of plant microfibres. In one variant, the absorbent strips 24 consist of synthetic fibres.

According to the first embodiment shown in FIG. 1, each absorbent strip 24 includes a first end 26 and a second end 28. The first end 26 of each absorbent strip 24 is, advantageously, arranged on the pole 30 of a sphere. Each absorbent strip 24 extends from the pole 30 along a longitude of the sphere.

Typically, the absorbent strips 24 are shaped by means of the pressure of the gas flow on the absorbent strips 24.

The gas flow production organ 18 is advantageously aimed at the pole 30 of the sphere. The gas flow production organ 18 is arranged on the concave side of the sphere, below the latter.

In one variant, the gas flow production organ 18 is placed upstream of the absorption organ 16. The term "upstream" refers here to the normal flow of the liquid in the device 10.

The gas flow production organ 18 is, e.g., a fan 18.

The injection organ 20 has a liquid injection tube 32. The injection tube 32 is, e.g., a tube that is open on both ends. One of the ends delimits an input 34 of liquid, and is connected to the reservoir 14. The opposite end delimits an ejection opening 36 of the injection tube 32. The ejection opening 36 is arranged near the first end 26 of each absorbent strip 24. The injection organ 20 comprises a dosing pump 38.

The operation of the device 10 according to the first embodiment of the invention will be described below.

Initially, a user enters into the computer 22 set points for the flow rate of the liquid to inject via the dosing pump 38 and the flow rate of the air flow produced by the fan 18. The liquid is initially stored in the reservoir 14.

Then, the liquid injection organ 20 pumps, via the dosing pump 38, the liquid from the reservoir 14 through the injection tube 32 up to the ejection opening 36.

Then, the liquid exits the injection tube 32 via the ejection opening 36, and is then absorbed by the absorbent strips 24 of the absorption organ 16. Thus, the liquid is injected into the first end 26 of each absorbent strip 24, and flows along each absorbent strip 24 towards the second end 28 of each absorbent strip 24.

Simultaneously, the air flow is generated by a fan 18. The air flow is directed at the pole 30 of the sphere formed by the absorbent strips 24. The fan 18 is advantageously arranged on the concave side of the sphere, inside the sphere, or below the latter.

Lastly, the liquid retained in the absorbent strips 24 of the absorption organ 16 is evaporated by means of the air flow directed towards the absorbent strips 24.

The absorbent strips 24 of the absorption organ 16 provide a substantial evaporation surface, and their arrangement with respect to one another facilitates the passage of the air flow, and thus substantial evaporation of the liquid retained in the absorbent strips 24.

Figure 2:
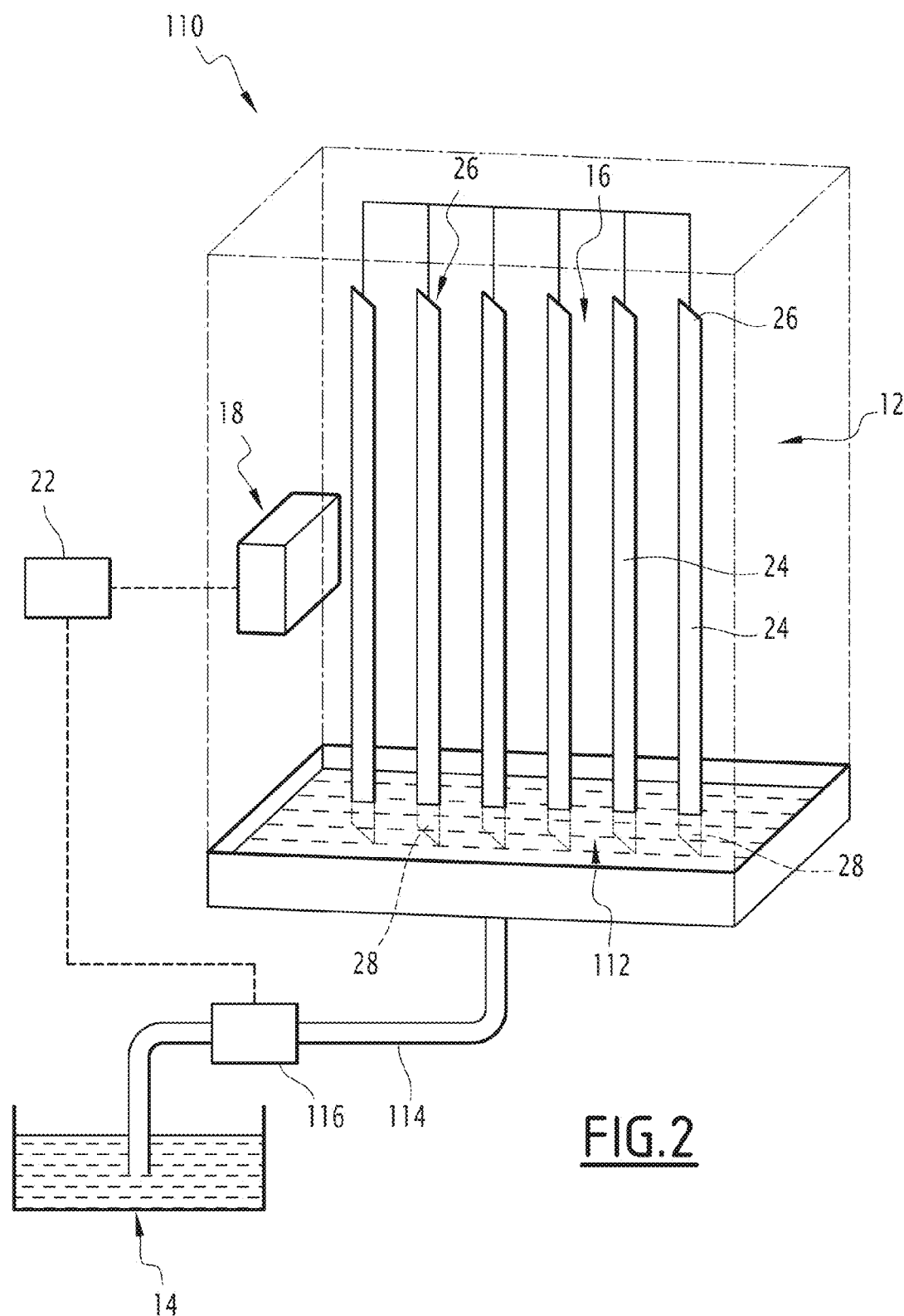

A second embodiment 110 of the device for evaporating a liquid according to the invention is schematically represented in FIG. 2.

Unlike the first embodiment shown in FIG. 1, the absorbent strips 24 are arranged parallel to one another, and extent along a vertical longitudinal axis.

Additionally, the device 110 according to the second embodiment comprises an organ for storing the liquid connected to the reservoir 14. The storage organ 112 is, e.g., a bucket arranged in the site 12 and in which the liquid is stored. The storage organ 112 is connected to the reservoir 14 via an injection tube 114, and advantageously comprises a dosing pump 116 connected to the computer 22.

The storage organ 112 is suited to store the liquid inside the site 12, and is advantageously arranged below the absorbent strips 24.

According to this second embodiment, the second end 28 of each absorbent strip 24 soaks in the liquid in the bucket 112. Each absorbent strip 24 thus absorbs the liquid by capillarity.

In this second embodiment, the fan 18 is advantageously arranged so as to generate a horizontal air flow towards the vertical absorbent strips 24. Thus, the air flow is perpendicular to the plane on which the absorbent strips 24 are contained.

Figure 4:
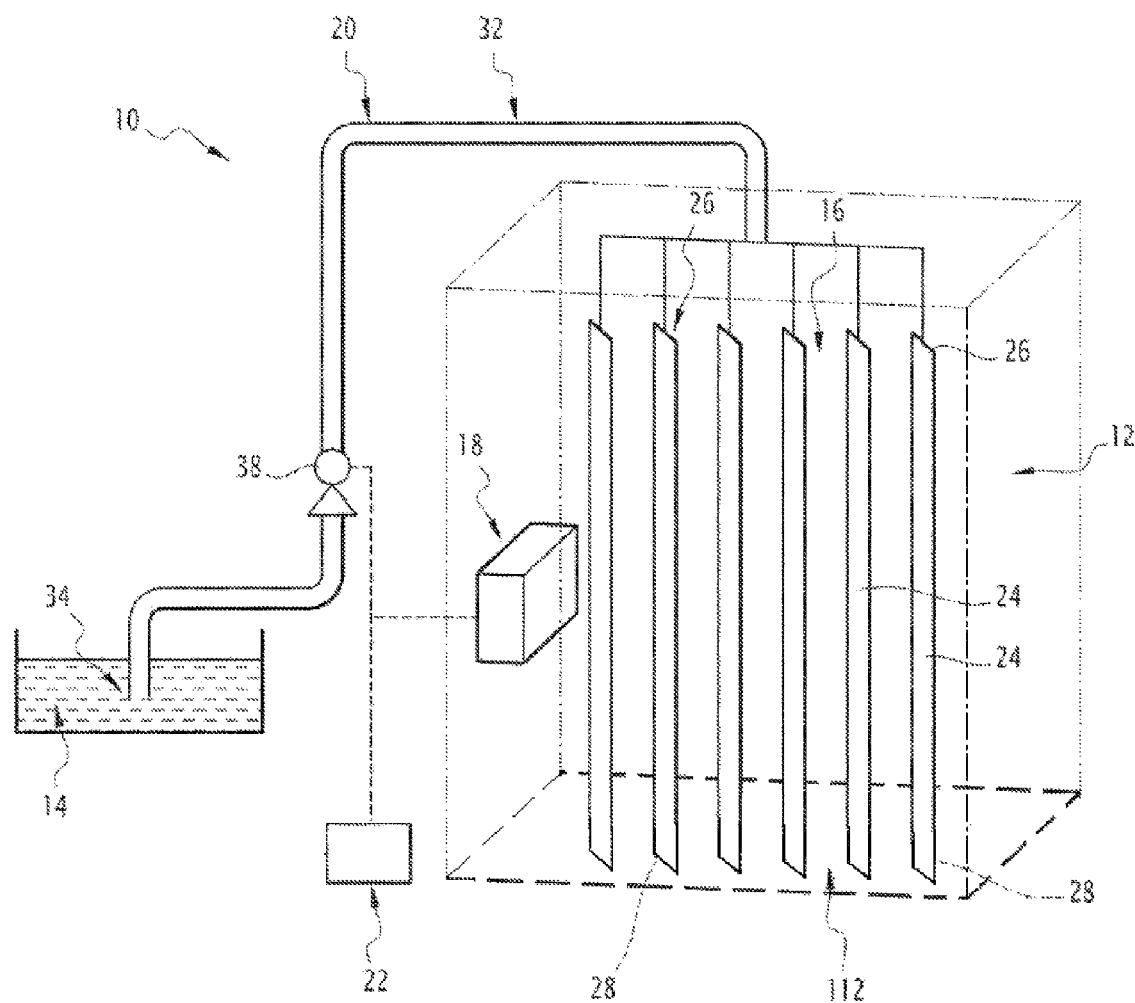

In one variant, the device 110 according to the second embodiment comprises the aforementioned injection organ 20. In this variant, which is schematically shown in FIG. 4, like the operation of the device 110 according to the first embodiment, the liquid is pumped from the reservoir 14 up to the ejection opening 36 of the injection organ 20 by a dosing pump. Additionally, the ejection opening 36 comprises a plurality of channels connecting the injection tube 32 to the first end 26 of each absorbent strip.

The liquid is then injected into the first end 26 of each absorbent strip 24, and flows vertically along each absorbent strip 24. The liquid is then evaporated by means of the horizontal gas flow aimed at the vertical absorbent strips 24.

Thus, it can be seen that the method and device for production of a gas flow according to the invention allow for the production of elevated concentrations of essential oil, possibly slightly below the saturation of the essential oil in the atmosphere, for long periods of time and large volumes.

The risk of condensation of the essential oil on the products stored, and thus the phytotoxicity of the essential oil, is thus avoided, because near the saturation the evaporation does not occur, and there is not risk of supersaturation.

Figure 3:
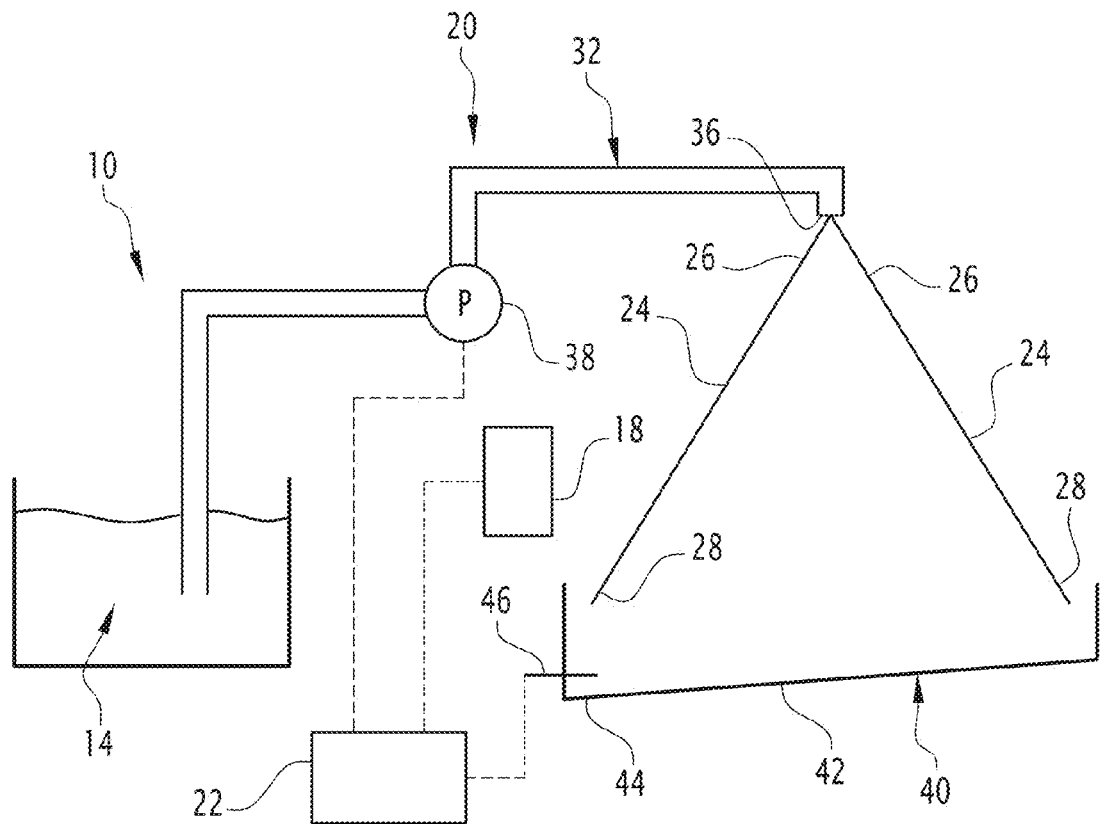

FIG. 3 depicts a variant of the first embodiment of the invention. Only the aspects by which the device and the method of the FIG. 3 differ from those of the FIG. 1 will be described below.

In the variant of the FIG. 3, each absorbent strip 24 forms an angle with the vertical direction and with the horizontal direction. The top first end 26 is located above the bottom second end 28. Each absorbent strip 24 extends substantially in a plane.

The absorbent strips 24 are not parallel to one another. For example the absorbent strips 24 are arranged by pair, the top first ends 26 of the absorbent strips of a given pair being located at the same point or close to each other. The space between the two absorbent strips 24 of a given pair increases when one follows the strips 24 from the top first end 26 to the bottom second end 28.

Each pair of absorbent strips has the shape of a V upside down, with the tip of the V pointing upward. The advantage of such an arrangement is that a single ejection opening 36 is sufficient to feed the liquid to the two absorbent strips.

The ejection opening 36 is for example equipped with an electrovalve controlled by the computer 22.

On the FIG. 3, only one pair of absorbent strips is depicted, but the device may include several pairs of absorbent strips. In this case, the injection tube 32 has one ejection opening 36 for each pair of absorbent strips.

According to a variant which is not depicted, the absorbent strips 24 are parts of a single sheet, folded along parallel horizontal lines in a fanfold or accordion manner.

The predetermined flow rate at which the liquid is injected in the absorbent strips 24 is automatically controlled at a set point.

The predetermined flow rate is controlled at said set point by the computer 22, or a calculator or any other similar device. The computer 22 acts on the injection organ 20 in order to control the predetermined flow rate.

Preferably, the predetermined flow rate at which the liquid is injected is chosen such that the liquid is entirely evaporated while flowing by gravity along the absorbent strips 24 towards the second ends 28 and no drop of liquid falls from the absorbent strips 24.

In this way, the quantity of liquid which is evaporated can be controlled in a very accurate manner. Said quantity corresponds exactly to the predetermined flowrate injected in the absorbent strips, and controlled by the computer 22. If drops of liquid fall from the absorbent strips, it means that the quantity of liquid which is evaporated is lower than the predetermined flowrate injected in the absorbent strips. It then becomes difficult to assess the quantity of liquid actually evaporated, and to accurately control said quantity.

It must be pointed out that for the sanitation a site or for treating food products in order to extend their preservation, the quantity of liquid actually evaporated must be accurately controlled to obtain good results.

As shown on the FIG. 3, drops of liquid falling from the absorbent strips 24 are automatically detected.

To that aim, a dripping pan 40 is arranged below the absorbent strips 24. The bottom 42 of the dripping pan 40 is arranged such that the drops falling from the absorbent strips 24 are collected by the dripping pan 40 and flow down to a sump 44. The dripping pan 40 is equipped with a liquid detector 46, arranged for detecting if liquid is present in the sump.

The liquid detector 46 is connected to the computer 22, and indicates to the computer 22 whether liquid is present in the sump or not.

If drops of liquid falling from the absorbent strips 24 are detected, the predetermined flow rate is reduced down to another predetermined flow rate at which drops of liquid do not fall from the absorbent strips.

Typically the computer 22 automatically reduces the predetermined flow rate. In a variant, an operator manually reduces the predetermined flow rate.

The invention claimed is:

1. A biocidal treatment method in which a liquid having biocidal properties is evaporated, comprising the following steps:

providing an absorption organ comprising a plurality of absorbent strips suited to retain the liquid, each absorbent strip having a top first end and a bottom second end;

injecting the liquid having biocidal properties into the first end of each absorbent strip, the liquid having biocidal properties flowing by gravity along the absorbent strip towards the second end, the liquid having biocidal properties being injected at a predetermined flow rate;

evaporating the liquid having biocidal properties by producing a gas flow directed towards the absorption organ at a temperature below 50° C., the gas flow with the evaporated liquid having biocidal properties being injected into a room in which plant matter are stored, wherein the liquid having biocidal properties is an active ingredient comprising at least one of an essential oil, a volatile synthetic product, pyrethrum, or synthetic pyrethrins, the liquid having biocidal properties is injected into the absorbent strips from a reservoir by an injection organ comprising a dosing organ, and wherein the predetermined flow rate at which the liquid having biocidal properties is injected is automatically controlled at a set point by acting on the dosing organ.

2. The method according to claim 1, wherein the/each essential oil is chosen from mint oil, clove oil, rose oil, thyme oil, oregano oil, or at least one of their constituents from the group of L-carvone, eugenol, geraniol, thymol, or carvacrol.

3. The method according to claim 1, wherein the liquid having biocidal properties comprises the at least one active ingredient dissolved in an organic solvent.

4. The method according to claim 1, wherein the dosing organ is a dosing pump.

5. The method according to claim 1, wherein the predetermined flow rate is controlled at said set point by a computer.

6. The method according to claim 1, wherein the predetermined flow rate at which the liquid having biocidal properties is injected is chosen such that the liquid having biocidal properties is entirely evaporated while flowing by gravity along the absorbent strip towards the second end and no drop of liquid having biocidal properties falls from the absorbent strip.

7. The method according to claim 1, wherein drops of liquid having biocidal properties falling from the absorbent strips are automatically detected, and the predetermined flow rate is reduced down to another predetermined flow rate at which drops of liquid having biocidal properties do not fall from the absorbent strips.

8. The method according to claim 5, wherein the evaporated liquid having biocidal properties is injected into a room, said set point being chosen such as to keep a concentration of said liquid having biocidal properties in an atmosphere of said room slightly below the saturation.

9. The method according to claim 1, wherein the first ends of the absorbent strips are arranged at a same given point, with each absorbent strip hanging from said given point such that the absorption organ has a concave shape.

10. The method according to claim 9, wherein the gas flow is directed toward the given point on a concave side of the concave shape.

11. The method according to claim 1, wherein the absorbent strips are arranged parallel to one another and extend along a longitudinal axis, which is perpendicular to the direction of the gas flow.

12. The method according to claim 1, wherein each absorbent strip consists of plant microfibres.

13. A biocidal treatment method In which a liquid having biocidal properties is evaporated, comprising the following steps:

providing an absorption organ comprising a plurality of absorbent strips suited to retain the liquid, each absorbent strip having a top first end and a bottom second end;

injecting the liquid having biocidal properties into the first end of each absorbent strip, the liquid having biocidal properties flowing by gravity along the absorbent strip towards the second end, the liquid having biocidal properties being injected at a predetermined flow rate; and evaporating the liquid having biocidal properties by producing a gas flow directed towards the absorption organ at a temperature below 50° C., wherein the predetermined flow rate at which the liquid having biocidal properties is injected is automatically controlled at a set point, and the evaporated liquid having biocidal properties is injected into a room, said set point being chosen such as to keep a concentration of said liquid having biocidal properties in an atmosphere of said room slightly below the saturation.

14. The method according to claim 13, wherein the liquid having biocidal properties comprises at least one active ingredient dissolved in an organic solvent.

15. The method according to claim 13, wherein drops of liquid having biocidal properties falling from the absorbent strips are automatically detected, and the predetermined flow rate is reduced down to another predetermined flow rate at which drops of liquid having biocidal properties do not fall from the absorbent strips.

16. The method according to claim 13, wherein the first ends of the absorbent strips are arranged at a same given point, with each absorbent strip hanging from said given point such that the absorption organ has a concave shape.

17. The method according to claim 13, wherein the absorbent strips are arranged parallel to one another and extend along a longitudinal axis, which is perpendicular to the direction of the gas flow.

18. The method according to claim 13, wherein each absorbent strip consists of plant microfibres.

\* \* \* \* \*